United States Patent [19]

Marinello

[11] 4,248,230

[45] Feb. 3, 1981

[54] SYSTEM FOR THE CURE OF INTERNAL WOUNDS AND INFLAMMATION OF HUMAN BODY, OF THE DIATHESIS, OF INTERNAL WOUNDS AND INFLAMMATION OF OCULAR APPARATUS, AND FOR STRENGTHENING OF HEALING POWER OF THE DRUGS AND BRAIN

[76] Inventor: Rosolino Marinello, Viale L. da Vinci 4, Mantova, Italy

[21] Appl. No.: 921,549

[22] Filed: Jul. 3, 1978

[51] Int. Cl.$^3$ ............................................. A61F 7/02
[52] U.S. Cl. ................................... 128/268; 424/195
[58] Field of Search ................ 128/268, 293, 260–262; 424/168, 195, 363, 364

[56] References Cited

U.S. PATENT DOCUMENTS

| | | | |
|---|---|---|---|
| 26,719 | 1/1860 | Titus | 128/268 |
| 98,875 | 1/1870 | Mays et al. | 424/195 |
| 914,935 | 3/1909 | Dunn | 128/268 |
| 3,644,620 | 2/1972 | Vittone | 424/195 |

OTHER PUBLICATIONS

Hackh, *Chemical Dictionary,* 3rd Ed., McGraw Hill, New York, 1944, pp. 553–554.
*Chemical Encyclopedia,* 5th Ed., Van Norstrand, New York, 1932, p. 598.
*Merck Index,* 7th Ed., Merck & Co., Rahway, N.J., 1960, pp. 37, 525, 696–697.

*Primary Examiner*—C. Fred Rosenbaum
*Attorney, Agent, or Firm*—Beveridge, DeGrandi, Kline & Lunsford

[57] ABSTRACT

Internal injuries, inflammations or diathesis are treated by applying preparations of allyl isothiocyanate to a dressing; placing the dressing on a cutaneous surface at the location of the internal injury, inflammation or diathesis; and exerting pressure on the pad to widen the pores of the cutaneous surface, to transfer the allyl isothiocyanate to the cutaneous surface, and to cause the medicament to penetrate through the cutaneous surface, to aid in increasing blood circulation to the injury, inflammation, or diathesis.

8 Claims, No Drawings

SYSTEM FOR THE CURE OF INTERNAL WOUNDS AND INFLAMMATION OF HUMAN BODY, OF THE DIATHESIS, OF INTERNAL WOUNDS AND INFLAMMATION OF OCULAR APPARATUS, AND FOR STRENGTHENING OF HEALING POWER OF THE DRUGS AND BRAIN

BACKGROUND OF THE INVENTION

This invention relates to a new drug and a new technique for obtaining new curative effects from the drug.

Almost every internal disease of man is due to internal inflammations or injuries. They result from physical, chemical or biological agents. The latter ones are by far the most important, such pathogenic biological agents including bacteria, protozoa, fungi and viruses, which give rise to infections. An infectious disease is therefore a morbid condition caused by pathogenic agents. It may be localized in a single part of the body or spread through every tissue by the blood flow.

Inflammation is a local reaction to the infection. It consists of a morphological alteration of inflammed tissues, so-called vessel congestion, which takes place in two stages, with ischemia, i.e. a local anemia produced by local obstacles to the arterial flow, followed by dilation and resulting hyperemia. The affected organism mobilizes phagocytes; they are transmitted through the blood to the site of inflammation and, together with local histiocytes (fixed macrophages), they struggle against pathogenic germs, trying to enclose, ingest and destroy them. Blood that is in such a phase has a throbbing character, gradually releasing its tension, achieving a kind of stasis with resulting congestion. In this second phase its components (erythrocytes and leukocytes which are usually mixed together) form two separated groups; erythrocytes being in the middle and leukocytes along the vessel walls.

From the dilated pores of the blood vessels the leukocytes and pathogenic germs seep into the tissues.

Vasodilatation, permeabilization and exudation follow an inflammation. The process of reparation and reconstruction, which takes place at the end of an inflammatory process, occurs according to a fixed pattern, i.e. the formation of granulation tissue.

An internal injury is, on the other hand, an anatomical damage of any internal tissue or organ of the body resulting from physical agents (fractures), chemical agents or pathogenic infection.

Diathesis is different from both inflammation and internal injury. It is a constitutional predisposition or tendency to a particular disease or affliction. Some men, through congenital or hereditary causes, have some organs or tissues, which are like a ground where certain diseases take root with greater facility. Diathesis, therefore, is not an actual morbid condition in itself, but a bodily constitution which is predisposed to a disease, or class of diseases. Lithic diathesis, for instance, describes the condition of men prone to the formation of calculi in the gall bladder, kidneys, vesica, prostate, and so on.

Since organic defenses are not always able to wipe out a morbifical attack, medical science has conducted a vast amount of research to find means to aid the body's defenses.

The aim of chemotherapy is the research and production of molecules which are as dangerous as possible to infectious agents and as harmless as possible to humans.

After the introduction of sera and vaccines, an important chemotherapeutic discovery was the preparation of sulfa drugs, whose effect is to reduce the activity of the metabolites of pathogenic germs, in order to weaken and make them easier prey of the natural defenses of organism. The discovery of antibiotics followed.

Antibiotic treatment takes advantage of manifestations of antagonism among different germs and different species, giving back the viable balance to the attacked organism. The action of antibiotics varies from antibiotic to antibiotic. Some interfere with the growth of micro-organisms and with cell division, some with microbial respiration, some with the utilization of essential metabolites.

Another kind of organic defenses against microbial infections or lesions is the use of drugs having therapeutic properties. These drugs are split up into two groups: elective and non-elective drugs, the former ones acting on certain organs or tissues, the latter ones on every organ or tissue.

In spite of the remarkable progress achieved in the treatment of internal injuries and inflammations by the introduction of new remedies, we are far, however, from achieving the final goal. Particularly, sulfa drugs and antibiotics, which proved invaluable in the treatment of acute infectious diseases are not very effective in the struggle against chronic diseases, for humans tend to assuetude in cases of a long-term treatment. Moreover, a specific remedy is lacking in many cases, such as in lithiasis and several organic disorders. Finally, there are some cases, in which, even though there are remedies for the treatment of certain diseases, their toxicity prevents their use at an adequate concentration. It follows that many diseases are still incurable. Also diathesis, being ignored rather than treated, too often fatally develops from a predisposition stage to a specific disease; and chronic infirmity as a permanent weakness threatens not only the health but the life itself of its victims.

The only refuge in many cases is to resort to a surgical operation. But, apart from not always being possible, it must be pointed out that, even when the operation is practicable, surgery often becomes a demolishing process, with a severe impairment of the functional capabilities of the patient.

The gaps touched on above, although they cover nearly every therapeutical field, are still more obvious for nervous and mental diseases. Here the treatment is highly ineffectual and often the only solution is a segregation of the patient from the human community.

To sum up, in spite of great progress, several deficiencies remain in the treatment of internal injuries and inflammations, of diathesis and of nervous and mental diseases.

The present invention compensates for some of the inadequacies of present-day therapy by the use of a chemical substance in conjunction with a special technique. The new discovery presupposes that in any microbic attack and in any dysfunction of the organs and tissues, the natural defenses constitute the base for defeating the illness and that medicines and remedies are merely subsidiary means of assisting such a defense. The corollary arrived at from this premise is that the principal task of therapy is not only to reinforce this reaction, but also to recreate it, by artificial means, when the body isn't able to do so independently.

On the basis of existing knowledge we can now provoke such a natural reaction in the superficial blood vessels. In fact it is known that heat administered by means of compresses, hydrotherapy, mud-baths, vapor or electricity on a part of the body produces a dilation of the superficial vessels and a consequent inflow of blood.

It is also known that certain substances other than heat have analogous characteristics. Various explanations have been formulated about the body's mechanism to produce this effect in response to the application of heat and revulsives. According to the oldest conception, their function was to eliminate the stanched blood and bad humors from the internal organs and to bring them to the surface.

According to the hypothesis of J. Mackenzie, every cutaneous area corresponds to a visceral area which is linked to sympathetic nerve connections. A stimulus, passing to and from a visceral segment by way of the spinal cord, can provoke corresponding vasomotorial reactions of a greater or lesser intensity which can contribute to the cure of a pathological condition.

Other theories attribute the function of these agents to the liberation of histamine to provoke the enlargement of the lumen of the vessels.

However, apart from these different explanations of the phenomenon, it is clear that while medicine has, until now, been able to provoke these reactions of the superficial vessels, it hasn't been able to produce a similar reaction for the deeper vessels of the human body.

SUMMARY OF THE INVENTION

The invention relates to a new composition and use of oil of mustard or of oil of horseradish (allyl isothiocyanate-$C_3H_5NCS$), the former one for normal patients and the latter for those suffering from neophrapathy. The drugs are applied by the use of a new technique for obtaining new curative effects. The new technique includes the following operations:

impregnate an absorbent dressing with a measured amount of the medicine;

apply the dressing to a cutaneous surface at the exact point overlying the injured, inflamed, or diathetic organ;

exert pressure on the dressing using the devices described in applicant's U.S. Pat. No. 4,036,229 or U.S. patent application Ser. No. 885,044 filed Mar. 9, 1978 or U.S. patent application Ser. No. 885,046 filed Mar. 9, 1978. The pressure produced by these devices is applied in such a way to get as near as possible to the external cutaneous surface of the body overlying the point of inflammation, or diathesis;

This procedure produces the following effects:

the squeezing of the dressing, and releasing the solution;

the widening of the pores of the skin subjected to pressure;

the penetration of the solution through the widened pores near the injured, inflamed or diathetic area.

As a result of the above factors, part of the medicine will reach the blood vessels serving the sick organ, provoking their enlargement, thereby producing an increased flow of blood with curative consequences.

DETAILED DESCRIPTION OF THE INVENTION

To increase the blood circulation to an injury, inflammation or diathesis, I propose a remedy utilizing a revulsive with a particular technique. This technique includes the following operations:

(1) Impregnate an absorbent dressing with a measured amount of the revulsive;

(2) Apply the dressing to the cutaneous surface at the exact point of the organ which is injured, inflammed, or affected by diathesis;

(3) exert pressure on the dressing using either the apparatus described in U.S. Pat. No. 4,036,229, dated July 19, 1977 or by using the small inflatable elastic pad described in U.S. patent application Ser. No. 885,044 filed Mar. 9, 1978. For illnesses regarding the eye socket and the brain one can use the orbital compression chamber, described in U.S. patent application Ser. No. 885,046 filed Mar. 9, 1978.

The pressure produced by the above mentioned devices should be applied in such a way as to get as near as possible to the external cutaneous surface of the body at the point of injury, inflammation or diathesis.

As a result of these operations one can expect the following effects:

(a) the squeezing of the dressing with the resultant expelling of the revulsive medicine;

(b) the widening of the pores of the skin subjected to pressure;

(c) the penetration of the medicine through the widened pores near the injured, inflammed, or diathetic area.

As a result of the above factors, after entering the pores the medicine will in part disperse into the bloodstream and in part reach the vessels serving the injured, inflamed or diathetic organ provoking their enlargement, thereby producing an increased flow of blood with curative consequences. One must observe the following precautions regarding the mode of operation:

(a') as the medicine is very toxic, it must be diluted and the concentration must be gradually intensified with the progression of the cure;

(b') during the course of the cure the pressure on the dressing must be increased gradually from an initial minimum, increasing in relation to the improvement of the lesion, inflammation or diathesis.

In order to most advantageously effect the enlargement of the blood vessels to aid in the rehabilitation of the affected tissue, a specific revulsive composition has been developed. This preferred revulsive uses the oil of mustard (allyl isothiocyanate-$C_3H_5CNS$ diluted in vegetable oil in a minimum ratio of 1 part of oil of mustard to 150 parts of vegetable oil up to a maximum ratio of 1 part oil of mustard to 50 parts vegetable oil for the treatment of wounds (including bone wounds), internal inflammation of the human body, and diathesis. The procedure is carried out according to the following directions:

(a) pour the dilution on an absorbent cotton wool pad dressing;

(b) lay the pad impregnated with the drug on the surface of the skin overlying the internally, inflamed, wounded or diathetic part;

(c) press the pad, by means of any of the above-identified apparatus for compressing the pad on the affected region of the body (excluding the orbital compression chamber) in order to get as near as possible to the injured, inflamed, or diathetic organ.

The use of these devices will press the skin in toward the injured part, dilate the pores of the skin, and release the revulsive from the dressing by squeezing the dressing. The devices also act to force the revulsive into the open pores in proximity to the inflamed, wounded, or diathetic organ, to provoke the opening of the blood veins and arteries of the wounded, inflamed, or diathetic organ or tissue and provide a greater blood flow for curative purposes.

For the treatment of wounds or inflammation of the eye apparatus of the brain, the oil of mustard (allyl isothiocyanate-$C_3H_5CNS$ should be diluted in vegetable oil in a minimum ratio 1/250 (1 part oil of mustard and 250 parts of vegetable oil) up to a maximum ratio 1/80. The procedure is carried out according to the following directions:

(a) Pour the dilution on two absorbent cotton wool dressings;

(b) Mount the two pads on the orbital compression chamber (described in U.S. patent application Ser. No. 885,046 filed Mar. 9, 1978). Inflate the apparatus as described in the application in order to expose the external orbital surface to pressure. The squeezing of the two dressings causes them to release the drug through the open pores of the skin submitted to pressure in the proximity of the wounded or inflammed part of the ocular or brain apparatus, thus provoking the opening of the veins and arteries and a greater blood flow to the wounded or inflamed organ for curative purposes.

When used in conjunction with another drug such as an antibiotic the diluted oil of mustard (allyl isothiocyanate-$C_3H_5NCS$), when applied as above provides a greater blood flow to the wounded, inflammed, or diathetic part and a greater absorption of the elected drugs.

For patients suffering from nephropathy, a composition containing oil of the horseradish, cochlearia armoracia of the family of the Cruciferae, (allyl isothiocaynate—$C_3H_5NCS$) may be diluted in vegetable oil in the proportions given above for the same purpose and with some directions for the healing of internal wounds, inflammations and diathesis.

It has also been found that oil of mustard and oil of horseradish may be combined and diluted in vegetable oil for the same purposes and with the same direction as indicated above. It should be remembered that the concentration of the drug should be gradually intensified relative to the improvement of the illness; and the pressure exerted by the above-mentioned apparatus should gradually and progressively increase from an initial minimum, the rate of increase being relative to the rate of healing of the wounds, inflammation or diathesis.

I claim:

1. A composition of matter for aiding in the increase of blood flow to an internal injury, inflammation or diathesis consisting of one part of oil of mustard and from 50 to 150 parts of vegetable oil.

2. A composition of matter for aiding in the increase of blood flow to an internal injury, inflammation or diathesis consisting of one part of oil of mustard and from 80 to 250 parts of vegetable oil.

3. A composition of matter for aiding in the increase of blood flow to an internal injury, inflammation or diathesis consisting of one part of oil of horseradish and from 50 to 150 parts of vegetable oil.

4. A composition of matter for aiding in the increase of blood flow to an internal injury, inflammation or diathesis consisting of one part of oil of horseradish and from 80 to 250 parts of vegetable oil.

5. A composition of matter for aiding in the increase of blood flow to an internal injury, inflammation or diathesis consisting of oil of mustard, oil of horseradish and vegetable oil.

6. A composition of matter for aiding in the increase of blood flow to an internal injury, inflammation or diathesis consisting of oil of mustard, oil or horseradish and 80–250 parts vegetable oil.

7. A method of treating internal injuries, inflammations or diathesis comprising the steps of (a) applying a solution containing one part allyl isothiocyanate and 50–150 parts of vegetable oil to a dressing, (b) positioning said dressing on the cutaneous surface overlying said internal injury, inflammation or diathesis, and (c) exerting sufficient pressure on said dressing to force said cutaneous surface inward towards said injury, inflammation or diathesis, to enlarge the pores of said cutaneous surface and to force said solution into said pores to aid in increasing blood circulation to said internal injury, inflammation or diathesis.

8. A method of treating internal injuries, inflammations or diathesis comprising the steps of applying a solution containing one part allyl isothiocyanate and 80–250 parts of oil to a dressing, (b) positioning said dressing on the cutaneous surface overlying said internal injury, inflammation or diathesis, and (c) exerting sufficient pressure on said dressing to force said cutaneous surface in-ward towards said injury, inflammation or diathesis, to enlarge the pores of said cutaneous surface and to force said solution into said pores to aid in increasing blood circulation to said internal injury, inflammation or diathesis.

* * * * *